US00PP13152P2

(12) United States Plant Patent
Meilland

(10) Patent No.: US PP13,152 P2
(45) Date of Patent: Oct. 29, 2002

(54) HYBRID TEA ROSE PLANT NAMED 'MEIDEBENNE'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/697,350

(22) Filed: Oct. 27, 2000

(51) Int. Cl.[7] ..... A01H 5/00
(52) U.S. Cl. ..... Plt./140
(58) Field of Search ..... Plt./140, 139, 130

(56) References Cited

PUBLICATIONS

UPOV–ROM GTITM Computer Database 2001/04, Aug. 6, 2001, GTI Jouve Retrieval Software, Citation for Rosa 'Meidebenne'.*

Protection Des Obtentions Vegetales, Bulletin officiel du Comité de la Protection des Obtentions Végétales, Nos. 8 and 9 (1999), Cover Pages and pp. 332, 334, 336 and 340.

* cited by examiner

*Primary Examiner*—Bruce R. Campell
*Assistant Examiner*—June Hwu
(74) *Attorney, Agent, or Firm*—Burns, Doane, Swecker & Mathis, LLP

(57) ABSTRACT

A new and distinct variety of Hybrid Tea rose plant is provided which forms attractive double very dark red blossoms that lack fragrance. The stems are strong. The plant exhibits an erect growth habit, dense semi-glossy dark green foliage, and very good disease resistance. The new variety is particularly well suited for producing cut flowers under greenhouse growing conditions.

1 Drawing Sheet

SUMMARY OF THE INVENTION

Figures 1, 2, 3, 4, 5, 6, 7, 8, 9, 10, 11, 12, 13, 14, 15, 16:
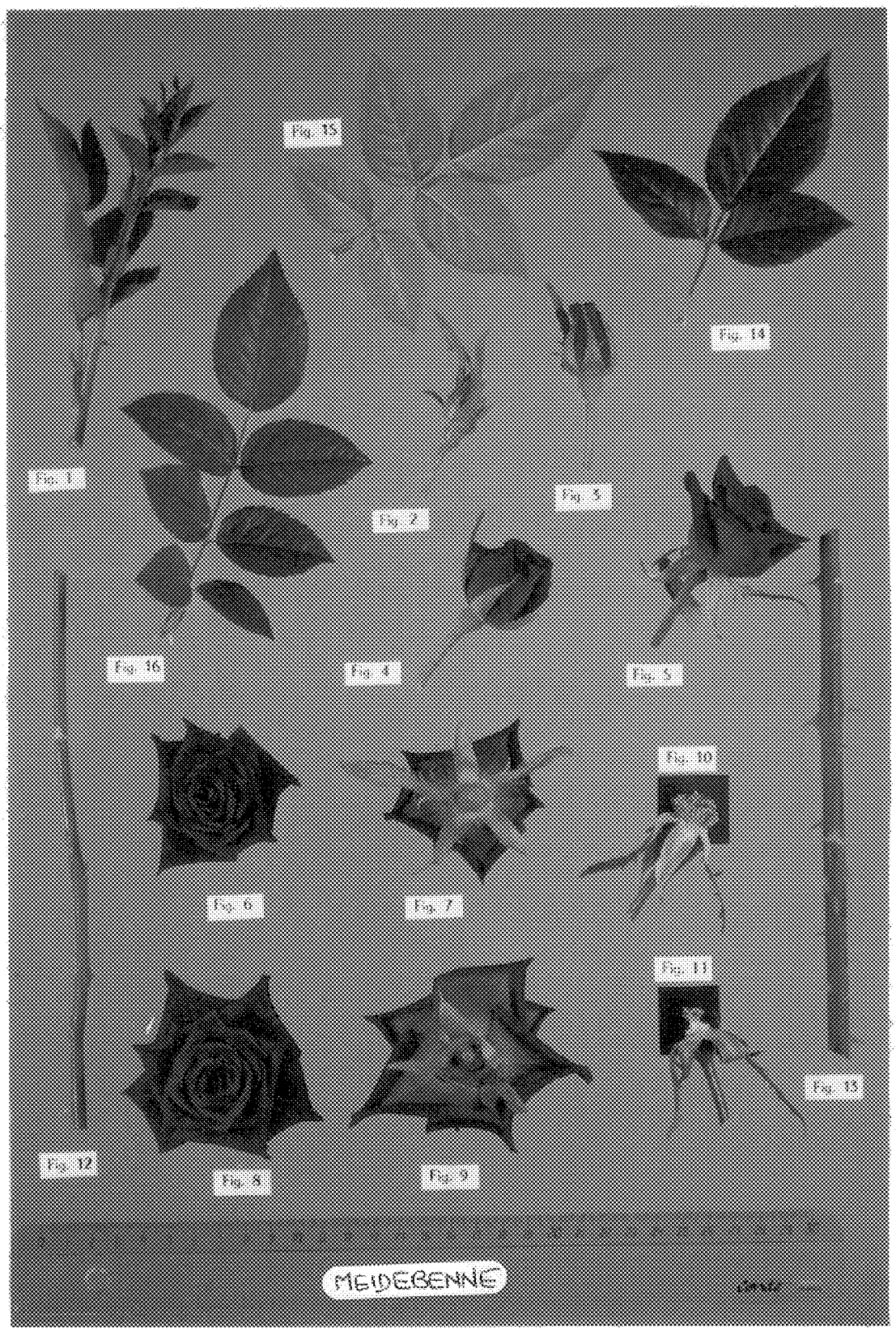

The new variety of *Rosa hybrida* Hybrid Tea rose plant was created by artificial pollination wherein two parents were crossed which previously had been studied in the hope that they would contribute the desired characteristics. The female parent (i.e., the seed parent) of the new variety was formed by crossing the 'Meifota' variety (U.S. Plant Pat. No. 5,683). The male parent (i.e., the pollen parent) was the 'Meilouzou' variety (non-patented in the United States). The parentage of the variety can be summarized as follows:

'Meifota'×'Meilouzou'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) exhibits an erect growth habit, (b) forms strong stems, (c) forms attractive double very dark red blossoms, (d) forms dense dark green semi-glossy foliage, and (e) is particularly well suited for cut flower production under greenhouse growing conditions.

The disease resistance of the new variety is excellent.

The new variety of the present invention can be readily distinguished from its parental varieties. For instance, the 'Meifota' female parent is of the Intermediate Class and forms medium pink blossoms. The 'Meilouzou' male parent displays considerably more thorns and unlike the new variety of the present invention forms external petals that sometimes exhibit burn discoloration.

The new variety well meets the needs of the horticultural industry and can be used to advantage to form cut flowers indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meidebenne' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during July while budded on *Rosa indica* understock and growing in greenhouses at Le Cannet des Maures, Var, France. Dimensions in centimeters are indicated at the bottom of the photograph.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates a specimen of a leaf with five leaflets — plan view — under surface; and FIG. 16 — illustrates a specimen of a leaf with seven leaflets — plan view — upper surface.

DETAILED DESCRIPTION

The chart used in the identification of the colors is that of The Royal Horticultural Society (R.H.S. Colour Chart). The description is based on the observation of two year-old plants during July while budded on *Rosa indica* understock and growing in greenhouses at Le Cannet des Maures, Var, France. The coloration in more common terms precedes reference to the chart in some instances. Such terminology is to be accorded its ordinary dictionary significance.

Class: Hybrid tea.

Plant:

*Height.*—When pruned to a height of 85 cm, floral stems having a length of approximately 70 to 80 cm in length commonly are produced.

*Width.*—Approximately 60 to 70 cm on average at the end of the growing season.

*Habit.*—Erect.

Branches:

*Color.*—Young stems: near Yellow-Green Group 147B. Adult wood: near Green Group 137B.

*Thorns.*—Size: medium (as illustrated) and approximately 0.8 cm in length on average. Quantity: moderately numerous (as illustrated). Color: near Yellow-Green Group 146D on young stems and adult wood, near Yellow-Green Group 146D. Configuration: elongated and curved downwards on the upper surface and concave on the under surface.

Leaves:

*Stipules.*—Adnate, pectinate, Green Group 137C, and approximately 3 cm in size on average.

*Petioles.*—Upper surface: slightly glandular and near Green Group 137C with anthocyanin coloration on new foliage slightly lighter than Greyed-Purple Group 187A. Under surface: with a few prickles and near Green Group 137C with anthocyanin coloration on new foliage slightly lighter than Greyed-Purple Group 187A.

*Leaflets.*—Number 3, 5, 7 (most often). Shape: somewhat ovate with an acuminate tip and a rounded base. Serration: simple and regular (as illustrated). Texture: smooth on both surfaces. General appearance: very dense, dark green, and semi-glossy. Color (young foliage): upper surface: near Green Group 137A with anthocyanin coloration of near Greyed-Purple Group 187A. under surface: near Yellow-Green Group 138B with anthocyanin coloration of near Greyed-Purple Group 187A. Color (adult foliage): upper surface: near Green Group 139A. under surface: near Greyed-Green Group 191A.

Inflorescence:

*Number of flowers.*—Usually one flower per stem.

*Peduncle.*—Long, with prickles, near Yellow-Green Group 144A, and the length is approximately 10 cm on average.

*Sepals.*—Upper surface: tomentose, near Green Group 138B and sometimes with anthocyanin coloration of near Greyed-Purple Group 187C on the edges. Under surface: smooth, medium green, near Yellow-Green Group 144A commonly two sepals having extensions of any significant length. Size: approximately 5 cm in length.

*Buds.*—Shape: conical. Size: medium. Length: approximately 4 cm on average.

*Flower.*—Shape: high-pointed center. Diameter: approximately 11 cm on average. Color (when opening begins): Upper surface: Cardinal Red, near Red Group 53A and 53B. Under surface: Cardinal Red, Red Group 53A. Color (when blooming): Upper surface: Currant Red, Red Group 46A and 46B, with a smooth aspect. Under surface: Cardinal Red, near Red Group 53A suffused with Red-Purple Group 60A. Color (at end of opening): Upper surface: Currant Red, Red Group 46A and 46B with a velvety smooth aspect. Under surface: Cardinal Red, near Red Group 53A suffused with Red-Purple Group 60A. Color of petal base: Upper surface: Near Red Group 46A and 46B with a velvety aspect. Under surface: near Red Group 53A suffused with Red-Purple Group 60A. Petaloids: a few petaloids (e.g., approximately 4 in number) sometimes are present. During November, these were near Greyed-Purple Group 187B in coloration with Greyed-Yellow Group 162A on the edge. Fragrance: none. Lasting quality: long, approximately 10 days on the plant and approximately 12 to 14 days when cut and placed in a vase. Petal texture: velvety. Petal shape: rounded base and tip with reflexed edges. Petal margin: smoothly rounded without extensions. Petal size: inside petals are approximately 5.5 cm in length on average and approximately 6 cm in width on average. Petal number: approximately 45 on average. Petal drop: good, the petals detach cleanly. Stamen number: approximately 110 on average. Anthers: near Red Group 51C, bordered with Yellow-Orange Group 22B and approximately 0.3 cm in size. Pollen: present and yellow in coloration. Filaments: near Red Group 51B and approximately 0.7 cm in length on average. Pistils: approximately 90 on average. Stigmas: near Red Group 54A. Styles: near Yellow Group 11B and approximately 1 cm in length. Receptacle: near Yellow-Green Group 144A in coloration, and funnel-shaped in longitudinal section.

Development:

*Vegetation.*—Strong.

*Blooming.*—Abundant.

*Resistance to diseases.*—Very good with respect to Powdery Mildew and Botrytis.

*Resistance or susceptibility to insects.*—Nothing noteworthy observed.

*Aptitude to bear fruit.*—Excellent, however, characteristics have not been observed since cut flowers have been primarily produced on plants to date.

*Hardiness.*—Not evaluated since the variety has been observed under greenhouse growing conditions to date.

I claim:

1. A new and distinct variety of Hybrid Tea rose plant characterized by the following combination of characteristics:

(a) exhibits an erect growth habit, (b) forms strong stems, (c) forms attractive double very dark red blossoms, (d) forms dense dark green semi-glossy foliage, and (e) is particularly well suited for cut flower production under greenhouse growing conditions;

substantially as herein shown and described.

* * * * *

MEIDEBENNE